(12) United States Patent
Kaufman et al.

(10) Patent No.: US 10,432,903 B2
(45) Date of Patent: *Oct. 1, 2019

(54) 3D LASER PROJECTION, SCANNING AND OBJECT TRACKING

(71) Applicant: FARO Technologies, Inc., Lake Mary, FL (US)

(72) Inventors: Steven P. Kaufman, Hooksett, NH (US); Kari J. Mettinen, Tilton, NH (US); Masoud Mohazzab, Andover, MA (US); Arkady Savikovsky, Burlington, MA (US); Joel H. Stave, New Boston, NH (US)

(73) Assignee: FARO TECHNOLOGIES, INC., Lake Mary, FL (US)

( * ) Notice: Subject to any disclaimer, the term of this patent is extended or adjusted under 35 U.S.C. 154(b) by 185 days.

This patent is subject to a terminal disclaimer.

(21) Appl. No.: 15/805,618

(22) Filed: Nov. 7, 2017

(65) Prior Publication Data

US 2018/0063497 A1 Mar. 1, 2018

Related U.S. Application Data

(63) Continuation of application No. 15/242,879, filed on Aug. 22, 2016, now Pat. No. 9,826,207, which is a
(Continued)

(51) Int. Cl.
*H04N 9/31* (2006.01)
*G02B 5/136* (2006.01)
(Continued)

(52) U.S. Cl.
CPC ............. *H04N 9/3194* (2013.01); *B23Q 7/00* (2013.01); *G01B 11/14* (2013.01); *G01N 21/94* (2013.01);
(Continued)

(58) Field of Classification Search
CPC ...... G01S 17/89; G01S 7/4802; G01S 7/4811; G01S 7/497; G01S 3/786; G01V 8/20;
(Continued)

(56) References Cited

U.S. PATENT DOCUMENTS 5,651,600 A 7/1997 Dorsey-Palmateer
6,547,397 B1 4/2003 Kaufman et al.
(Continued)

FOREIGN PATENT DOCUMENTS

JP 2009028819 A 2/2009
JP 2009526211 A 7/2009
(Continued)

*Primary Examiner* — Tri T Ton
(74) *Attorney, Agent, or Firm* — Cantor Colburn LLP

(57) ABSTRACT

A laser projection system is provided. The laser projection system includes at least one laser projector having a laser source and a laser detector. The system includes processors for executing computer instructions, the processors are coupled to the laser projector, the computer readable instructions include determining the component is stationary based on the emitting of a first laser light towards a reference target on the component and receiving a portion of the first laser light by the laser detector. In response to the determining the component is stationary: determining a transformation for mapping a first coordinate system of the laser projector to a second coordinate system of the component and forming a visual pattern on the component. The computer instructions further include determining that the component is in motion based on receiving a portion of the first laser light by the laser detector and removing the visual pattern.

10 Claims, 6 Drawing Sheets

Related U.S. Application Data continuation of application No. 14/642,160, filed on Mar. 9, 2015, now Pat. No. 9,423,278.

(51) Int. Cl.
  *B23Q 7/00* (2006.01)
  *G01B 11/14* (2006.01)
  *G01N 21/94* (2006.01)
  *G01S 3/786* (2006.01)

(52) U.S. Cl.
  CPC .............. *G01S 3/786* (2013.01); *G02B 5/136* (2013.01); *H04N 9/3129* (2013.01); *H04N 9/3161* (2013.01); *H04N 9/3185* (2013.01); *G01N 2201/10* (2013.01)

(58) Field of Classification Search
  CPC .. G03B 21/00; G03B 21/142; G03B 21/2086; G08G 1/052; G01B 11/24; G01B 11/14; G01N 21/94; G01N 2201/10; G02B 5/136; H04N 9/3129; H04N 9/3161; H04N 9/3194; H04N 9/3185; B23Q 7/00
  See application file for complete search history.

(56) References Cited

U.S. PATENT DOCUMENTS

| | | |
|---|---|---|
| 7,306,339 B2 | 12/2007 | Kaufman et al. |
| 7,555,404 B2 | 6/2009 | Brennan et al. |
| 8,085,388 B2 | 12/2011 | Kaufman et al. |
| 8,582,087 B2 | 11/2013 | Kaufman et al. |
| 9,826,207 B2 * | 11/2017 | Kaufman ............... G02B 5/136 |
| 2006/0232791 A1 | 10/2006 | Turrini |
| 2017/0041582 A1 | 2/2017 | Kaufman et al. |

FOREIGN PATENT DOCUMENTS

| | | |
|---|---|---|
| KR | 1020110083128 | 7/2011 |
| WO | 2009061620 A1 | 5/2009 |

* cited by examiner

Response from the Two Retro-Targets on Tracking Projector

3D LASER PROJECTION, SCANNING AND OBJECT TRACKING

CROSS-REFERENCE TO RELATED APPLICATIONS

The present application is a continuation application of U.S. application Ser. No. 15/242,879 filed on Aug. 22, 2016, which is a continuation application of U.S. application Ser. No. 14/642,160 filed on Mar. 9, 2015, now U.S. Pat. No. 9,423,278.

FIELD OF THE DISCLOSURE

This disclosure relates to the field of laser projection, and more particularly, to techniques for three-dimensional (3D) tracking of the motion of parts, and projecting laser patterns onto the parts based on the detected position of the parts with respect to the laser.

BACKGROUND

A laser projection system includes a laser beam steering device capable of determining the projector's location and orientation in 3D space with respect to the coordinate system of an object. Laser projectors are widely used in manufacturing processes to assist in precision assembly of large scale structures, composite articles, etc. For instance, glowing visual templates generated by laser projection are used in production assembly processes to assist in the precise positioning of parts, components, and the like on any flat or curvilinear surfaces. Laser projection also enables other information to be displayed onto the work surface, such as operator instructions, part numbers, and three-dimensional visualization of components. Presently laser projection technology is widely used in manufacturing of composite parts, in aircraft and marine industries, or other large machinery assembly processes, truss building, and other applications. Laser projection provides the ability to eliminate expensive hard tools, jigs, templates, and fixtures typically used for placement of materials and components. Laser projection also offers flexibility and integration of the assembly process with computer aided design (CAD) data.

In a laser-assisted assembly process, an operator positions component parts by aligning some features (e.g., edges, corners, etc.) of the part with the glowing template. After the part positioning is completed, the user fixes the part with respect to the article being assembled. The person assembling the article uses his or her eyesight to make a judgment about proper alignment of the part to the glowing template. Because this process relies on the visual judgment of a worker, it is subjective, and its quality may be substantially reduced by human errors. Human errors may adversely impact any manufacturing process, and therefore revealing such errors promptly can help avoid or reduce costly and time-consuming corrective measures. In aircraft manufacturing, for example, every production step is verified and documented. One hundred percent quality assurance is often required. Therefore, techniques that combine the capabilities of laser projection with immediate verification of part placement during the assembly process are desirable.

BRIEF DESCRIPTION OF THE DRAWINGS

The accompanying drawings are not intended to be drawn to scale. In the drawings, each identical or nearly identical component that is illustrated in various figures is represented by a like numeral.

BRIEF DESCRIPTION

Figure 1:
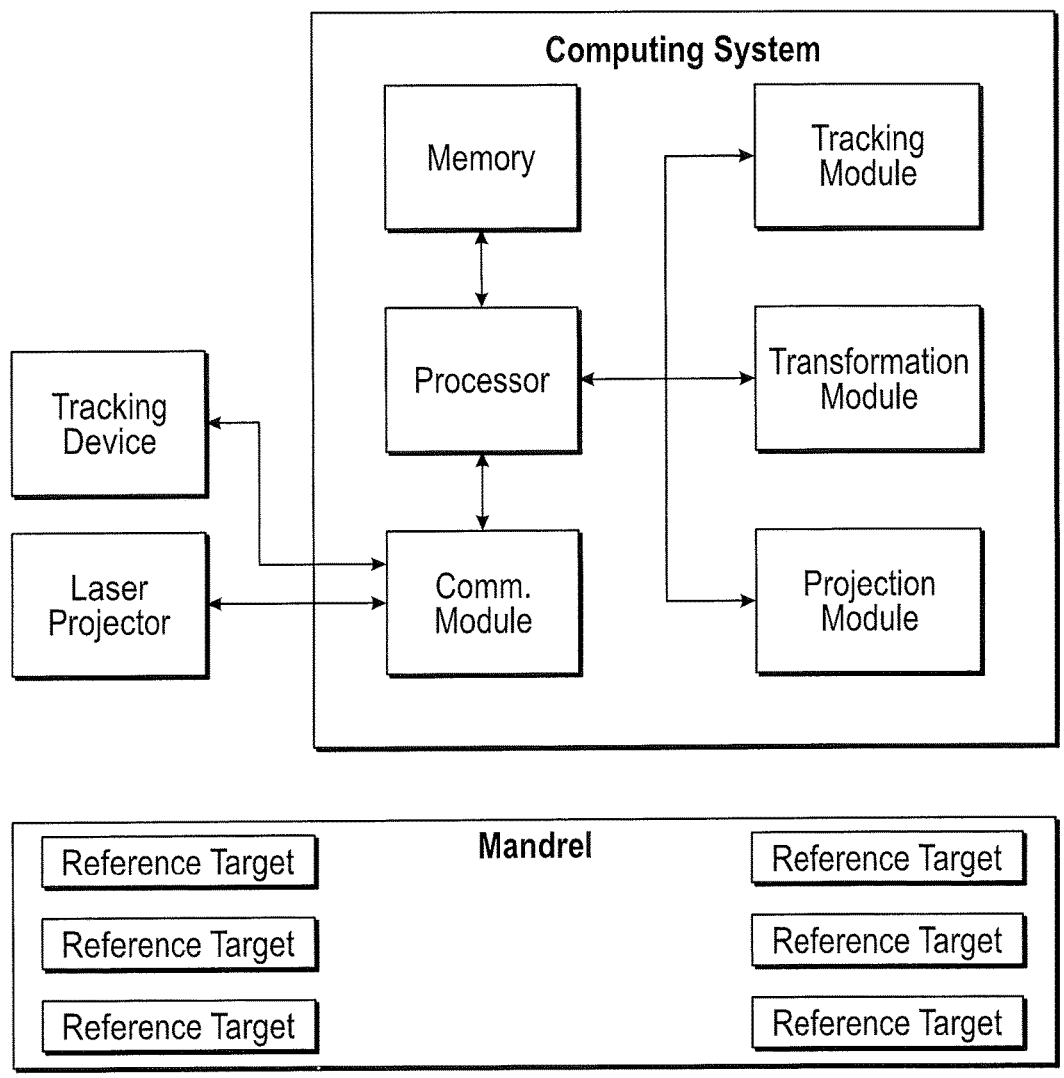
FIG. 1 is a block diagram of an example laser projection system, in accordance with an embodiment of the present disclosure.

According to one aspect of the invention, a laser projection system is provided. The laser projection system includes at least one laser projector having a laser source and a laser detector. The system includes one or more processors for executing non-transitory computer readable instructions, the one or more processors operatively coupled to the laser projector, the non-transitory computer readable instructions that include determining the component is stationary based at least in part on the emitting of a first laser light toward at least one reference target on the component and receiving a portion of the first laser light by the laser detector. In response to the determining the component is stationary: determining a transformation for mapping a first coordinate system of the laser projector to a second coordinate system of the component and forming a visual pattern on the component based at least in part on the transformation. The computer instructions further include determining that the component is in motion based at least in part on receiving a portion of the first laser light by the laser detector and removing the visual pattern from the component.

DETAILED DESCRIPTION

Techniques are disclosed for tracking the position of moving parts and assemblies using 3D laser projection, and projecting templates and other information onto the parts and assemblies based on position. The projected template may then be used, for example, to assist in fabrication of the assembly by indicating where to put a next component or layer, or to assist in post-fabrication inspection of the assembly by indicating where the various components or layers should have been placed. In the latter case, note that a range or tolerance about the parts placement location can be provided so deviation of the actual placement location from the parts location can be readily determined and compared to a specification or requirement, as the case may be. Numerous other embodiments and applications will be apparent in light of this disclosure.

General Overview

Ply layup, for example, is an important and labor intensive task in composite based parts manufacturing. In certain manufacturing industries, such as aerospace and construction, components of a part or assembly are constructed by precision placement of composite layers. Such precision is important for ensuring the integrity of the part or assembly.

In many cases, the composite layers are applied manually on mandrels. To the extent that laser projection might be used in some approaches, the task of re-alignment after the part and tools are moved or rotated must be performed manually by finding reference targets in the field of view and then bucking-in to them, and further involves a number of non-trivial issues. Such problems are exacerbated with very large assemblies that are moveable in a multi-dimensional space. In any case, this continuous manual buck-in process is a tedious and cumbersome task that may result in mistakes and reduced productivity.

To this end, and in accordance with an embodiment, a 3D laser projection system is provided for tracking the position of moving parts and assemblies, and projecting templates and other information onto the parts and assemblies based on position. Each time the assembly is moved to a new position to continue the manufacturing process, the laser projector searches for available targets in its field of view and automatically bucks-in and continues its projection for further layup or assembly processing (or inspection, as the case may be). For example, for parts laid on a mandrel, which rotates around a cylindrical axis, operators may apply layers of composite in certain precise directions over the part or mandrel using visual patterns projected from a laser projector onto the part or mandrel surface. The operators occasionally rotate the mandrel to access a different region of the part, and then stop mandrel rotation to continue applying new composite layers or continuation of the composite layer or some other component or feature of the item being built. In accordance with an embodiment, the laser projectors will stop projecting light when the mandrel starts to rotate. Meanwhile, a tracking device (e.g., another laser projector or machine vision system) continues tracking the rotation, thereby allowing for automatic bucking-in to the coordinate system of the assembly when rotation stops. This process of mandrel rotation and stopping is repeated until the required part is fully assembled or constructed. Subsequently, in the case of composite materials, the layers are compressed by a process known as vacuum bagging. The part is then moved to an autoclave, where temperatures of up to 1,000 Fahrenheit and pressures near 125 pounds per square inch are applied for a period of several hours or until the composite is cured with very high tensile strength. At this time, the composite turns into a solid structure and, after some other post processing, is ready for paint and integration.

One or more laser projectors can be configured to aim laser light beams on a part or other work piece based on the position of the part relative to the laser projector(s). The position of the part is tracked as the mandrel rotates. Some existing mandrels include an encoder for detecting rotational position of the mandrel. However, interfacing to the rotation encoder in many instances requires proprietary interfacing, which may not be readily available. Therefore, in accordance with various embodiments, it is appreciated that tracking the mandrel using a laser projector or machine vision system is useful and practical and more precise in laser projection applications. In an embodiment, one laser projector is utilized for both tracking the position of a part and projecting patterns on the parts. In some other embodiments, at least two laser projectors are utilized. For example, at least one of the projectors may be dedicated to tracking the position of the mandrel or the position of the part, and at least one of the projectors may be dedicated to projecting a visual pattern onto the part based on the current position of the mandrel or part after movement. In other embodiments, the laser projector detects a so-called home position of the mandrel and any position of the mandrel after movement away from the home position using uniquely coded targets. In such embodiments, the laser projector tracks the coded targets as the mandrel moves by scanning along the expected target path and using reflection from the coded or otherwise known targets. In some embodiments, and as will be appreciated in light of this disclosure, note that position tracking of the mandrel can be carried out from the rotation encoder (assuming access to encoder interface), where position data is provided to the laser projector tasked with projecting the visual pattern onto the part based on the known current position, thereby allowing that projector to buck-in to the new position. In such example embodiments, note that laser projectors dedicated to tracking the mandrel or part may be used to supplement or replace the encoder-based position tracking if so desired for a given application.

In accordance with an embodiment, the transformation between the coordinate systems of the laser projector and the part being assembled can be obtained using specialized target reference points on the part. The positions of these reference points are precisely known in the part's coordinate system. The laser projector scans reference targets affixed to the mandrel, and solves non-linear equations to obtain projector orientation with respect to the part. In some cases, four targets are sufficient for performing a coordinate transformation calculation. However, it will be understood that using additional targets (e.g., six or more targets) can improve the precision with which the coordinate systems of the laser projector and the part are aligned. Generally, these targets should be stationary during the scanning process to recapture alignment for bucking-in purposes, as any movement or vibration of the target relative to the laser projector may result in poor alignment of the projected pattern and the part being assembled.

As noted above, during the assembly process, a mandrel or other fabrication tool upon which parts and materials are placed may be subject to movement as the process proceeds from the placement or layup of one part or component to the next. The fabrication tool can, in some embodiments, include a substantially cylindrical mandrel that rotates about a cylindrical axis, or an asymmetric tool, fixture or jig that moves in arbitrary directions. In some applications, for example, composite layers of material are wrapped over a relatively large cylindrical mandrel to form a part (e.g., many meters in length and/or many meters in diameter). The mandrel is occasionally rotated about the cylindrical axis, which passes through the centers of the mandrel bases, to allow additional composite material to be applied to the part by operators standing on a stationary work platform. The part is preferably completely stopped for alignment of the laser projector with the part. In such applications when parts are allowed to move in stop-and-go sequences, and the laser projector is stationary, the laser projection system can automatically re-align itself each time the part stops moving. The alignment process is also referred to in this disclosure as a buck-in process, and can be achieved in various ways as provided herein.

In some embodiments, retro-reflective reference targets affixed to an object can be used to reflect a laser beam back to a laser projection system for detecting position of the object and tracking movement of the object. Retro-reflective reference targets are useful in laser projecting systems because they provide a distinguishable optical feedback signal by returning a substantial portion of projected laser light back into the beam path through the beam steering system of the projector. The positions of these reference targets on the object are precisely fixed and known. The laser can then project a visual template or other information onto specific portions of the object with high positional precision (e.g., to within +/−0.015 inch). These visual templates and information are used by operators during the manufacturing process. When the object moves relative to the laser projection system, the position of the reference targets for laser projector alignment purposes will change. For instance, in one specific composite layup application, axially symmetric rotating mandrels are used for manufacturing the body of a cylindrical aerospace structure. Retro-reflective reference targets can be placed on the mandrels at regular angular separations (e.g., 10 degrees apart). Operators layup composite layers of material onto the mandrel. The mandrel is occasionally rotated to allow the operators to continue the layup on a different portion of the mandrel. Each time the mandrel is rotated, the operators need to know where to place the continuation of the layers. The reference targets let the projector know the new location so that an appropriate projected template can be provided at each position of the assembly process.

Such reference targets may include, for example, retro-reflective material, non-reflecting features (e.g., holes, edges, registration marks, etc.), spherical balls or tooling balls. These are intended to be non-limiting examples, and it will be understood that any physical feature of the mandrel or object that can be detected by the laser projection system can be used without departing from the scope of the present disclosure. Reference targets may be placed, for example, around the mandrel on or near one or both opposite ends of the outer cylindrical surface. In one such embodiment, reference targets are placed at regular angular intervals, as previously explained. The data for the reference targets and the data for the part surface are all known in the same coordinate system. The laser projector can be taught the home position for the mandrel. In another embodiment, the laser projector detects the home position using uniquely coded targets. As will be appreciated, a coded target is a target that reflects a unique light pattern back to the projector or is otherwise associated with a unique aspect that can be identified by the projection system (e.g., based on reflected data or image data). The laser projector tracks the coded targets as the mandrel moves by scanning along the expected target path and using reflection from the targets. In this embodiment the laser projector behaves as a tracking device.

In an embodiment, retro-reflective reference targets are placed near one or both opposite ends of an axially symmetric rotating mandrel or other fabrication tool (e.g., a rotating or sliding jig). The reference targets are spaced apart at regular angular intervals, such as, for example, intervals between about five and 20 degrees or greater, and in particular at intervals of about 10 degrees. In some cases, the reference targets are placed on or near each end of the mandrel such that at least three or four of the reference targets on each end are visible to the tracking device (e.g., a laser projector) at a given time. The laser projectors and the tracking device (to the extent it is separate from a laser projector in a given embodiment) are interconnected in a data communications network. A tracking device, which may be implemented with, for example, a laser projector or machine vision system, is configured to detect and track the reference targets in the field of view of the tracking device to determine whether the targets are stationary or moving, or have moved since the last observation. When the mandrel rotates, the laser projector stops projecting 3D shapes or other information, while the tracking device continues to track the reference targets. As the mandrel rotates, some reference targets may move out of the field of view of the tracking device, while other reference targets may enter the field of view.

When the laser projection system senses that the mandrel has stopped moving, the relative position of the laser projection system and the mandrel is updated by bucking-in to, for example, at least six reference targets (e.g., three targets on or near each end of the mandrel that are within the field of view of the tracking laser). The reference targets are used to register or buck-in the laser projection system. Target locations are known to the system such that the position of the mandrel can be determined when a target is detected. Other laser projectors being used in this process, if any, may receive (via the communication network) information from the tracking device about the new position of the mandrel, if they cannot generate this position information themselves as indicated in other example embodiments. The system can then buck-in to the new position of the mandrel using the targets located near one or both opposite ends of the mandrel. The projecting lasers can then project 3D shapes or other visual information onto the mandrel or work piece at the appropriate locations.

In some cases, the mandrel will rotate only forward or only backward, while in other cases it may rotate in any combination of forward and backward. In any such cases, the tracking device determines the direction and the degree of rotation of the mandrel. In some cases, uniquely coded targets are placed around the mandrel at arbitrary angles around the axis of rotation. Each target reflects back light indicative of its code. Angular rotation of the mandrel can thus be determined based on the known positions of each coded target. The tracking device scans the coded targets and interprets the absolute angle of the mandrel with respect to a pre-established home or origin position.

In another embodiment of this disclosure, a vision system with its geometry known with respect to a plurality of laser projectors is used to remotely observe the angle of the mandrel or a moving assembly and trigger the update of the laser projection alignment to the object. Alternatively, or in addition to, the vision system can be used to remotely observe the visual image codes associated with each reflector on the moving assembly (e.g., "reflector 6" or "REFL_1" labels positioned adjacent a corresponding reflector), with each such image label associated with a pre-established or otherwise known position on the assembly thereby allowing for laser projection alignment to the object. The image code can be captured by a camera or other imaging device (included in the vision system) and then processed (e.g., using optical character recognition, or so-called OCR) to access position data associated with the image. As will be further appreciated, such a visual image-based coded target scheme can be used as an alternative to a coded target scheme that reflects back coded light, with either process allowing target positions to be determined.

In another embodiment of this disclosure, the mandrel rotation angle is tracked using laser or vision tracking systems and laser traces are projected on already placed plies for inspecting their placement for accuracy with respect to, for example, direction, orientation, and straightness. As will be appreciated, the projected template effectively creates a visual marker that can be used to assess deviation from ideal placement. The deviation can be determined manually (e.g., by visual inspection of an operator) or automatically (e.g., by machine vision or other suitable inspection tool).

Numerous other embodiments and variations and applications will be apparent in light of this disclosure.

System Architecture

FIG. 1 is a block diagram of an example laser projection system, in accordance with one example embodiment of the present disclosure. The laser projection system includes a computing system, which controls one or more laser projectors and tracking devices. The laser projector is configured to direct a laser light beam toward a mandrel or other fabrication tool used during an assembly or manufacturing process. The tracking device is configured to detect positions of reference targets affixed to or formed in the mandrel. This position information allows the laser projection system to buck-in to any position the assembly can take. The computing system includes one or more processors configured to execute the methods as variously disclosed herein. While the tracking device is shown as separate and distinct from the laser projector, it will be appreciated in light of this disclosure that the tracking device and the laser projector may be co-located such that one unit provides both tracking and projecting functions.

The processor(s) may include a microprocessor, microcontroller, an application-specific integrated circuit, or one or more programmable integrated circuits such as a field-programmable gate array or complex programmable logic device, or the like. Instructions for performing the methods may be stored in a memory or other non-transient storage medium. The memory may include any of the available types of memory, such as random access memory, FLASH memory, a hard disk drive, a solid-state drive, or any combination of these. The memory may also receive and store image data for projection onto a work object, which may be laid upon the mandrel or fabrication tool. The memory is operatively connected to the processor(s) via a wire or bus, or in some cases externally via serial or parallel connection, or wirelessly via WiFi, Bluetooth, or the like. Any number of suitable processor-memory schemes can be used, as will be appreciated, and the present disclosure is not intended to be limited to any particular one.

The computing system includes several modules for performing certain functions as variously described herein. For example, a tracking module may be configured to receive tracking data from the tracking device that includes positions of the reference targets in a first coordinate system fixed with respect to the mandrel or fabrication tool. A transformation module may be configured to calculate a transformation for mapping the first coordinate system to a second coordinate system fixed with respect to the laser projector(s) based on the detected position of the reference targets. A projection module can receive CAD or other image data and generate commands to project a visual pattern onto the mandrel or part. The preceding modules may be implemented in software stored in the memory, or as separate physical logic components of the computing system, or any combination of these. The functionality of each of these modules is described in further detail below.

The computing system also includes a communications module that transmits commands to, and receives data from, the laser projector(s) and tracking device(s). Communication between the communications module and the laser projector(s) and tracking device(s) can occur via wired network and device connections, such as Ethernet or USB, or communication can occur wirelessly via Wi-Fi, Bluetooth, or other appropriate wireless communication format. The communications module interfaces with the processor(s) via a wire or bus, or in some cases externally via serial or parallel connection, or wirelessly via Wi-Fi, Bluetooth, or the like.

Figure 2A:
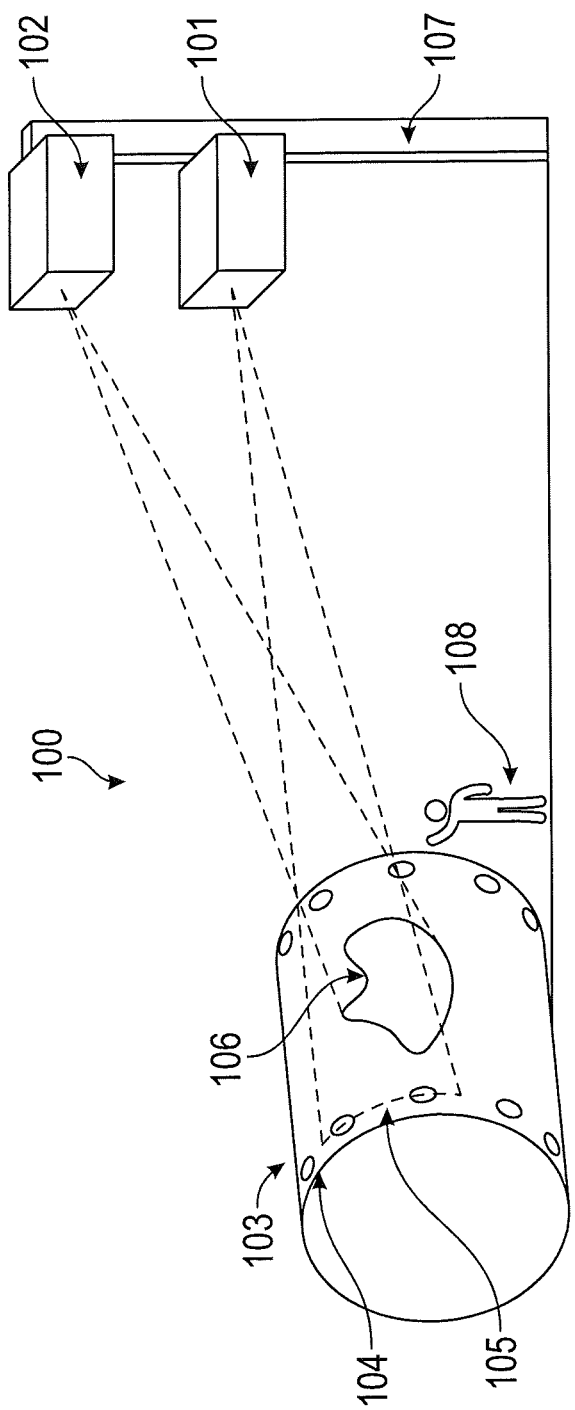
FIGS. 2A and 2B show an example laser projection system in a manufacturing environment, in accordance with an embodiment of the present disclosure.
Figure 2B:
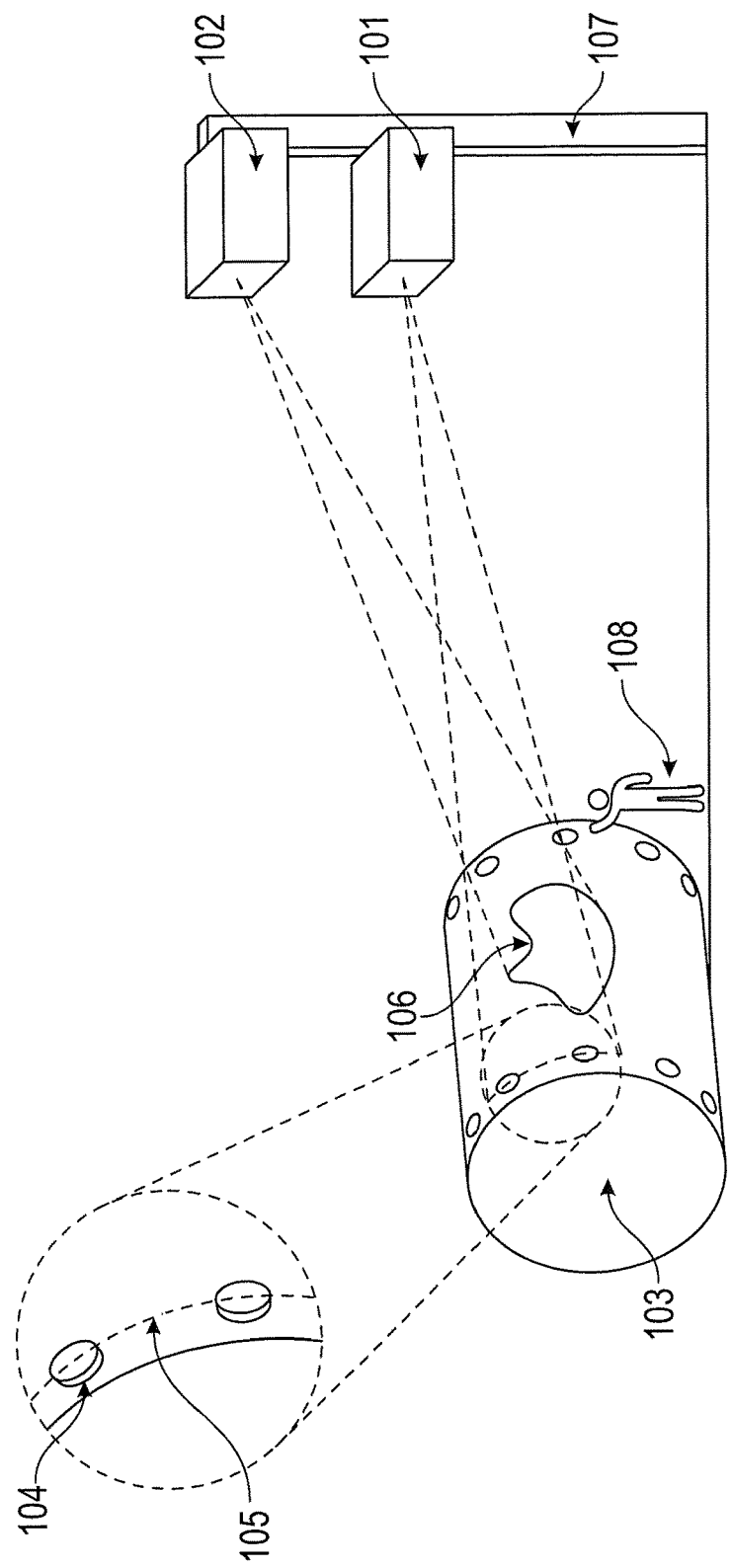

FIG. 2A shows an example laser projection system 100 in a manufacturing environment, in accordance with an embodiment. FIG. 2B shows a portion of the example system 100 of FIG. 2A in further detail. The system 100 includes a mandrel tracking laser projector 101 and a scanning laser projector 102 that can be used in conjunction with an assembly layout process. FIG. 2B also shows a rotating cylindrical mandrel 103 having several reference targets 104 located near one or both opposite ends of the mandrel 103. It will be understood that the mandrel 103, the reference targets 104, or both are not necessarily part of the laser projection system 100 in some embodiments. One or more posts 107 may support the tracking device 101 and the scanning projector 102 at various locations relative to the mandrel 103. For example, the tracking device 101, the scanning projector 102, or both may be located at some fixed distance away from the mandrel 103 and at a height sufficient to allow the laser to project onto the mandrel 103 without substantial interference by other objects or persons. In an embodiment, the laser projectors 101, 102 are placed at a height of about six meters from the ground facing toward the mandrel 103. The tracking device 101 may be placed in any location to avoid any accidental blocking of the laser light on the mandrel.

During assembly, an operator 108 works beside the mandrel 103 to place composite layers onto the mandrel 103 to form a so-called composite layup. The term layup may also generally refer to the process of assembling a part formed of composite materials. A visual pattern 106 can be projected onto the mandrel 103 by the scanning projector 102 while the mandrel 103 is stationary. The operator 108 can use the pattern 106 as a visual reference for positioning the material on the mandrel 103. As the layup progresses, the operator 108 rotates the mandrel 103 from time to time. The pattern 106 may vary depending on the position of the mandrel 103 relative to the laser projection system 100. For instance, a first pattern may be projected onto the mandrel 103 while the mandrel 103 is stationary in a first position, and a different second pattern may be projected onto the mandrel 103 while the mandrel 103 is stationary in a second position that is different than the first position. The movement and position of the mandrel 103 is detected by the tracking device 101, as will be described in further detail below. In this manner, the pattern 106 automatically changes as the operator rotates the mandrel 103.

In some embodiments, the tracking device 101 includes a laser and a laser detector. In other embodiments, the tracking device 101 includes a machine vision system. In cases where the tracking device 101 is a laser projector, the tracking device 101 is configured to project a beam of laser light onto one or more of the reference targets 104, which in turn reflect the laser light back to the tracking device 101. A laser trace region 105 represents a region of the mandrel (e.g., one end of the mandrel) upon which the tracking device 101 can project the laser. The tracking device 101 uses the light reflected from one or more of the reference targets 104 located within the laser trace region 105 to track the position of the mandrel 103 relative to the scanning projector 102. In some embodiments, the reference targets 104 include a retro-reflective material affixed near one or both opposite ends of the mandrel 103. The retro-reflective material may be formed such that it produces a particular pattern of reflected light as the laser scans the surface of the target 104 or as the target 104 moves with respect to the laser (e.g., such as the example coded target 500 shown and described with respect to FIG. 5). Such reference targets are referred to in this disclosure as coded targets. However, it will be understood that, in some embodiments, the reference targets 104 are not necessarily coded targets, and further that the retro-reflective material can be configured to reflect light in any manner that is detectable by the tracking device 101. In some embodiments, the reference targets 104 are defined by one or more physical features of the mandrel 103, such as edges or holes, or other materials, such as magnets affixed to the mandrel 103, any or all of which can be used by the tracking device 101 to track the position of the mandrel 103. For example, the tracking device 101 may detect the presence or absence of laser light reflected from the surface features of the mandrel at a given angle of the projected laser beam. In some cases, a combination of retro-reflective targets, coded targets, magnetic targets and mandrel features may be utilized for tracking the position of the mandrel 103.

Figure 2C:
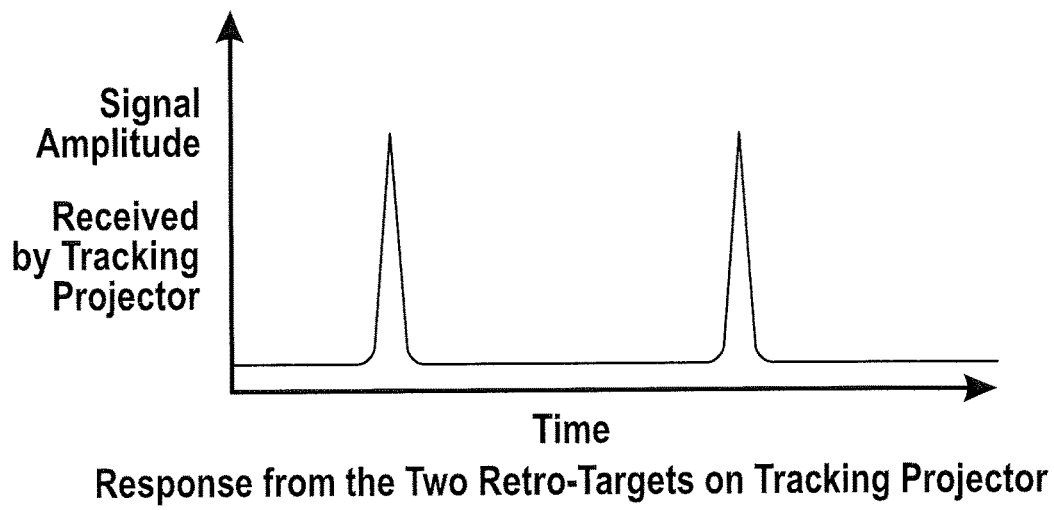
FIG. 2C shows an example signal response graph of the laser projection system of FIGS. 2A and 2B, in accordance with an embodiment of the present disclosure.

According to an embodiment, the tracking device 101 continually directs a laser trace line toward the laser trace region 105, such that the laser trace line covers at least one of the reference targets 104. As the mandrel 103 rotates, the tracking device 101 senses motion of the mandrel 103 and commands the scanning projector 102 to stop the projection of the visual pattern 106. Then, while the mandrel 103 rotates, the tracking device 101 measures the motion of reference targets 104 as they move through the laser trace region 105. FIG. 2C shows an example signal response graph of the laser projection system of FIGS. 2A and 2B, in accordance with an embodiment of the present disclosure. The signal response represents the detection of each of the reference targets 104 as a function of time while the reference targets 104 are moving, where the amplitude of the signal increases (e.g., spikes) as the targets are detected within the field of view of the tracking device 101, and where the distance between the spikes depends on the speed of target movement. Therefore, by measuring the motion of the reference targets 104, the tracking device 101 can calculate an updated rotational position of the mandrel 103. When the mandrel 103 stops rotating, the tracking device 101 bucks in to the current rotational position of the mandrel 103 using, for example, at least six visible reference targets in the new field of view based on the data encoded on the targets. The information about the new position and buck-in targets are communicated to the scanning projector 102. The scanning projector 102 scans the reference targets in the updated field of view and aligns to the new rotational angle of the mandrel 103 and begins projecting the visual pattern 106 that corresponds to the current position.

In another embodiment, the system 100 includes a tracking laser projector 101 and multiple scanning laser projectors 102. The mandrel tracking is done by a tracking laser projector 101, and when the mandrel 103 stops moving, parts are placed onto the mandrel 103. The scanning laser projectors 102 then scan the surface for inspection. The scanning projectors 102 will inspect the direction of ply layup and its precision.

In another embodiment, the scanning laser projector 102 scans the surface of mandrel 103 for detection of unwanted foreign object debris (FOD). Upon detection of FOD, a laser projector 102 will highlight the FOD by projecting laser traces on the FOD's perimeter and projects warning signs for operators. In some embodiments, the tracking laser projector can also project on the part in a similar manner to the scanning laser projector 102.

In another embodiment, the tracking device 102 includes a machine vision system.

In some embodiments, mandrel tracking is performed using coded targets. However, it will be appreciated that mandrel tracking can be performed using tooling balls, photogrammetric targets, bushings holes, corners and edges features on assembly parts in addition to, or instead of, using coded targets.

Figure 3:
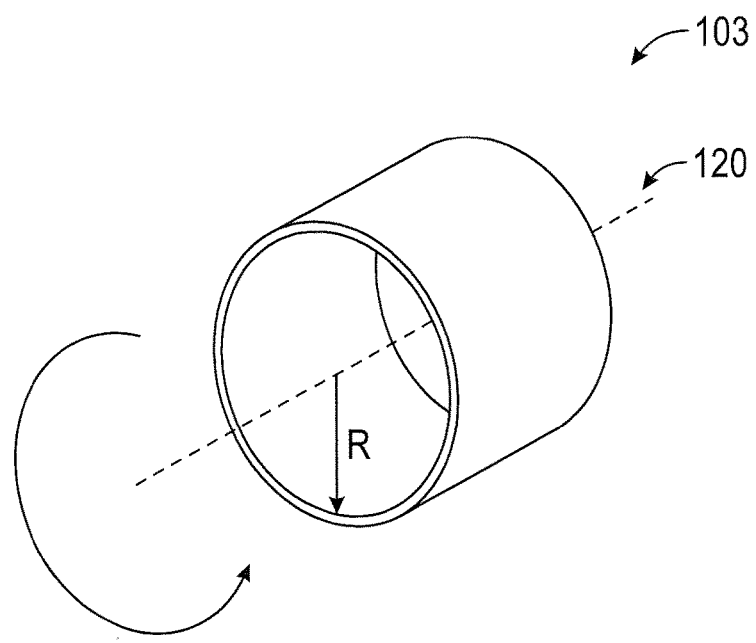
FIG. 3 depicts an example mandrel that can be used in a given fabrication process, in accordance with an embodiment of the present disclosure.

FIG. 3 depicts an example mandrel 103. The mandrel 103 is substantially cylindrical and has an axis 120 passing through the centers of the bases of the mandrel. The mandrel 103 is configured to rotate about the axis 120 in one or both directions. In some embodiments, the mandrel 103 is relatively massive and extends the length of a platform upon which one or more assemblers may stand while applying layers and/or components to the mandrel during an assembly process. The precise dimensions of the mandrel are not particularly relevant, to the extent that any size mandrel can be used in the context of the present disclosure. However, a massive mandrel presents alignment challenges, as will be appreciated in light of this disclosure.

Figure 4:
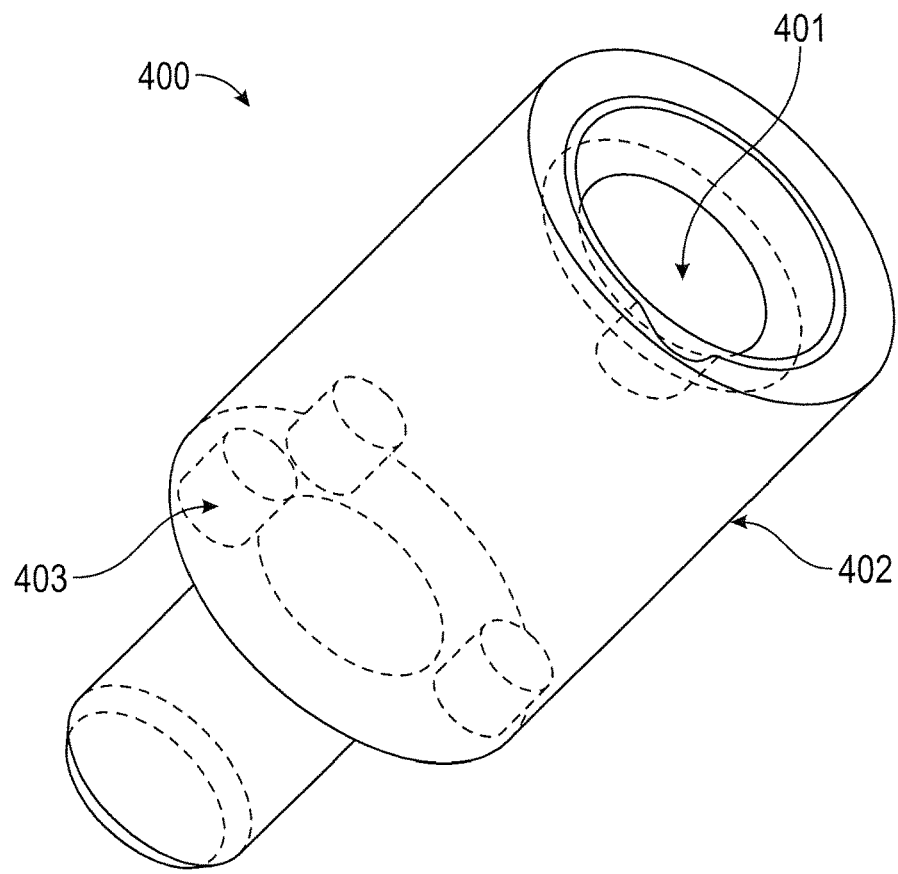
FIG. 4 shows an example magnetic target, in accordance with an embodiment of the present disclosure.

FIG. 4 shows an example magnetic target 400 placed on a stainless steel bushing in a mandrel, in accordance with an embodiment. The target 400 includes a retro-reflective material 401, a body 402, and a magnet 403 inserted at the shoulder base of the target 400. The retro-reflective targets 400 are placed around a mandrel (e.g., the mandrel 103 of FIG. 1) such that they are around a circle with regular angular spacing. Through holes are machined on a circle around the mandrel in which steel bushings are pressed in. Tooling targets used in this implementation have a shank and an opening for retro-reflective material. The targets rest on the bushings and are equipped with magnets so that they will stay on the surface even when they are facing down. In some cases, the targets are ¼" diameter disks.

In an embodiment, the reference targets are numbered clockwise and labeled based on their position on left side or the right side of the mandrel. The measurements are converted into the coordinate system of the mandrel. As the mandrel is axially symmetric, its coordinate system may be chosen such that the Y axis is along the axis passing through the center of the mandrel. The reference targets inserted in the bushings all have precisely known heights. Therefore, the position of each labeled target can be known within the coordinate system of the mandrel.

In an embodiment, the reference targets are placed approximately 10 degrees apart from each other near one or end of the mandrel. The target position x y z data, together with projection layer data and their surface normals, are provided to the software that runs the laser projectors.

Figure 5:
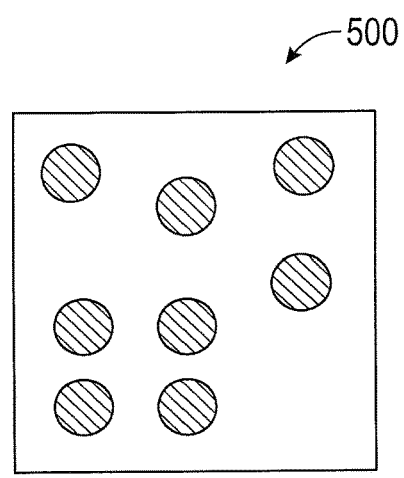
FIG. 5 shows an example coded target, in accordance with an embodiment of the present disclosure.

FIG. 5 shows an example coded target 500 with eight circular features are specific locations, in accordance with an embodiment. The number, shape, size, position, or any combination of these features may be varied to create differently coded targets. For example, the arrangement and relative positioning of the circular features may be different on different reference targets 104, and may be decoded by the tracking device 101 to represent different mandrel positions. In operation, the laser light that impinges on such coded targets is reflected back in a fashion that encodes the code of the target. Each code can be associated with a given location. Hence, the location of targets causing the various reflections can be known by the receiving device, thereby allowing for buck-in and continued template projecting onto the target-bearing assembly at its new position.

Example Methodology

Figure 6:
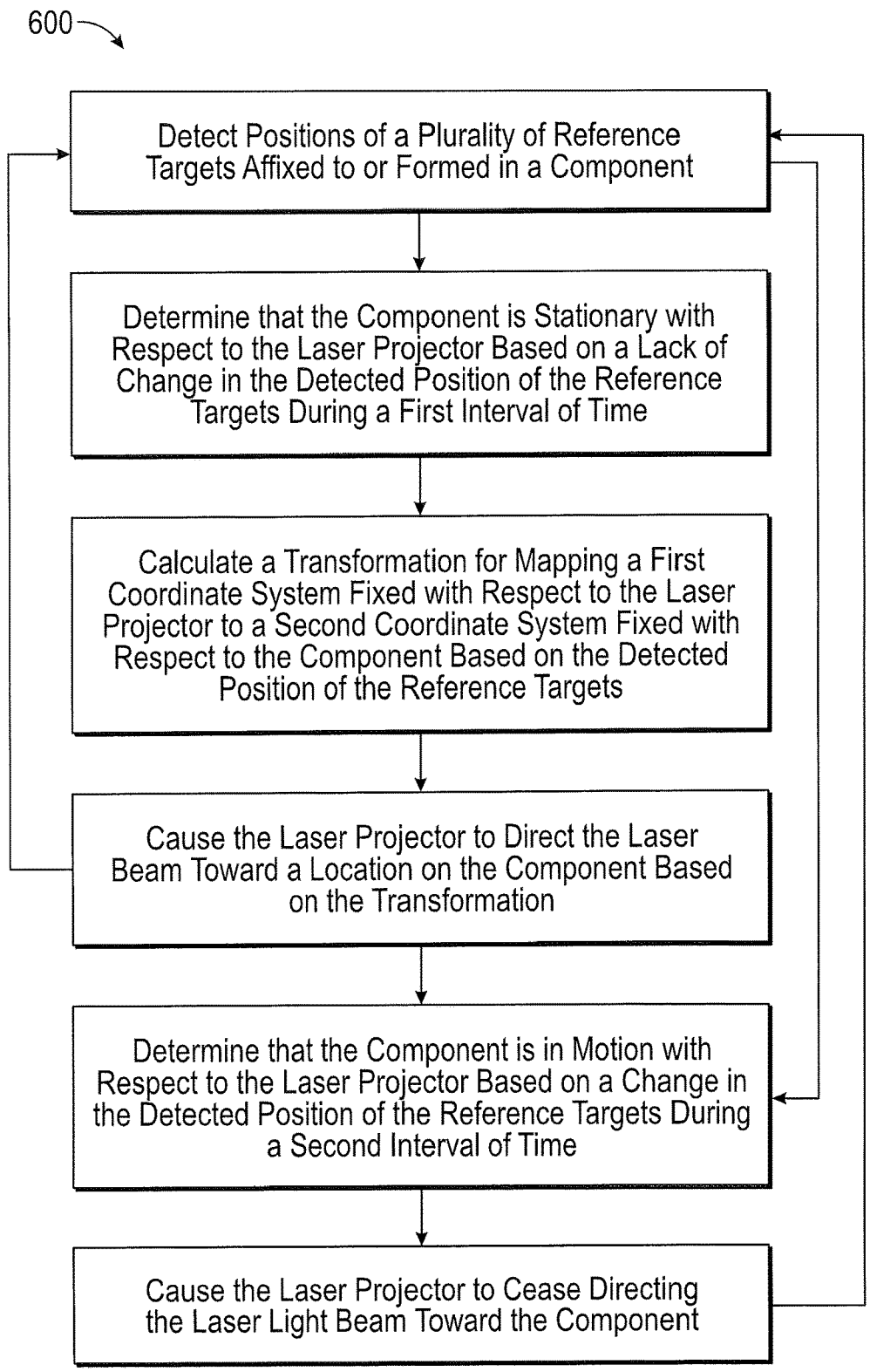
FIG. 6 shows a flow diagram of an example laser projection methodology, in accordance with an embodiment of the present disclosure.

FIG. 6 shows a flow diagram of an example laser projection methodology 600, in accordance with an embodiment. The methodology 600 can be implemented, for example, in the system 100 of FIGS. 2A and 2B, although any number of other embodiments for carrying out the methodology will be apparent in light of this disclosure. For example, the system may include a tracking device configured to detect (e.g., optically) positions of a plurality of reference targets affixed to or formed in a component (e.g., the mandrel 103, such as described with respect to FIGS. 2A and 2B), a laser projector configured to direct a laser light beam toward the component (e.g., for projecting a visual pattern onto the component, mandrel or part); and a processor operatively coupled to the tracking device and the laser projector. Recall that the laser projector and tracking device may be the same unit, wherein common laser projection platform is used for both tracking and template projection purposes. In any such cases, the processor can be configured to carry out the method 600.

As can be seen, the method 600 includes determining if the component is stationary with respect to the laser projector based on a lack of change in the detected position of the reference targets during a first interval of time. This may be accomplished, for instance, by noting that a reflected beam pattern has remained unchanged for a pre-established period of time (e.g., more than 3 seconds or so), or based on a cue received from a computer vision system indicating non-movement of the component, or any other motion sensing scheme. In response to the determination that the component is stationary, the method 600 continues by calculating a transformation for mapping a first coordinate system fixed with respect to the laser projector to a second coordinate system fixed with respect to the component based on the detected position of the reference targets, and causing the laser projector to direct the laser light beam toward a location on the component based on the transformation. As will be appreciated, this transformation allows the laser projector to buck-in to the coordinate system of the component to that laser light templates can be accurately placed onto the component to assist in manufacturing and inspection applications.

The method 600 further includes determining if the component is in motion with respect to the laser projector based on a change in the detected position of the reference targets during a second interval of time, which may be different than the first period of time. In response to a determination that the component is in motion, the method 600 continues by causing the laser projector to cease directing the laser light beam toward the component. It is noted that in the case where the tracking device includes a separate laser projector (e.g., other than the laser projector used to project visual patterns), the laser projector of the tracking device continues to direct the laser light beam toward the component (e.g., mandrel or part) for tracking movement of the component. In some cases, the component includes a fabrication tool (e.g., a mandrel or jig) or a part mounted on the fabrication tool (e.g., a composite layup). In some specific example such cases, the component is a cylindrical mandrel rotatable with respect to a cylindrical axis in the first coordinate system.

In some cases, the method 600 includes causing the laser projector to project a visual template or pattern onto the component while the component is stationary, the visual pattern adapted to facilitate manual assembly of parts or fabrication of parts on locations of the component that are within a field of view of the laser projector. Likewise, the visual pattern can be adapted to facilitate automatic assembly of parts or fabrication of parts on locations of the component that are within a field of view of the laser projector, using robots with machine vision that can detect the projected pattern. In a similar fashion, the visual pattern can be adapted to facilitate manual or automatic inspection of parts or fabrication of parts already placed on locations of the component that are within a field of view of the laser projector. In some cases, the tracking device includes a laser projector or a machine vision system. In some cases, the reference targets include retro-reflective surfaces affixed on or near opposite ends of the component, where positions of each of the retro-reflective surfaces are fixed within the first coordinate system. In such cases, the method 600 further includes detecting the position of the reference targets based on laser light reflected from at least two of the light reflective surfaces and the fixed positions of the retro-reflective surfaces. In some such cases, at least three of the reference targets are arranged in a row. In some other such cases, the retro-reflective surfaces are uniquely coded for obtaining the position of each reference target with respect to the first coordinate system. In some cases, the reference targets include non-reflective features formed in at least one of the component and a part laid on the component (e.g., edges, holes, spherical balls or tooling balls, to name a few examples).

The foregoing description and drawings of various embodiments are presented by way of example only. These examples are not intended to be exhaustive or to limit the present disclosure to the precise forms disclosed. Alterations, modifications, and variations will be apparent in light of this disclosure and are intended to be within the scope of the present disclosure as set forth in the claims.

What is claimed is:

1. A laser projection system comprising:
at least one laser projector having a laser source and a laser detector; and
one or more processors for executing non-transitory computer readable instructions, the one or more processors operatively coupled to the laser projector, the non-transitory computer readable instructions comprising:
determining the component is stationary based at least in part on the emitting of a first laser light toward at least one reference target on the component and receiving a portion of the first laser light by the laser detector;
in response to the determining the component is stationary:
determining a transformation for mapping a first coordinate system of the laser projector to a second coordinate system of the component; and
forming a visual pattern on the component based at least in part on the transformation; and
determining that the component is in motion based at least in part on receiving a portion of the first laser light by the laser detector and removing the visual pattern from the component.

2. The system of claim 1, wherein the component includes at least one of a fabrication tool and a part mounted on a fabrication tool.

3. The system of claim 1, wherein the component includes a cylindrical mandrel rotatable with respect to a cylindrical axis in the first coordinate system.

4. The system of claim 1, wherein the at least one laser tracker further comprises a machine vision system.

5. The system of claim 1, wherein:
the reference targets include a cylindrical body coupled to the component on one end and having retro-reflective surfaces affixed on an opposite end, wherein positions of each of the retro-reflective surfaces are fixed within the first coordinate system, and
the computer readable instructions further comprises detecting the position of the reference targets based on laser light reflected from at least two of the light reflective surfaces and the fixed positions of the retro-reflective surfaces.

6. The system of claim 5, wherein at least one and at most two of the reference targets are arranged in a row.

7. The system of claim 5, wherein the reference targets include a plurality of retro-reflective surfaces disposed in a pattern on the end of the reference target, wherein each of the reference targets includes a different pattern.

8. The system of claim 1, wherein the reference targets include non-reflective features formed in at least one of the component and a part laid on the component.

9. The system of claim 1, wherein the computer readable instructions further comprise:
   scanning the component with the laser projector with a third laser light beam; and
   detecting foreign object debris on the component.

10. The system of claim 9 wherein the computer readable instructions further comprise causing the laser projector to project a laser traces on a perimeter of the foreign object debris.

\* \* \* \* \*